United States Patent
Kanyuh et al.

(10) Patent No.: US 9,809,662 B2
(45) Date of Patent: Nov. 7, 2017

(54) POLYPROPYLENE PRODUCTION PROCESSES

(71) Applicant: UOP LLC, Des Plaines, IL (US)

(72) Inventors: Adam J. Kanyuh, Streamwood, IL (US); Michael J. Banach, North Barrington, IL (US); Robert B. James, Northbrook, IL (US)

(73) Assignee: UOP LLC, Des Plaines, IL (US)

( * ) Notice: Subject to any disclaimer, the term of this patent is extended or adjusted under 35 U.S.C. 154(b) by 155 days.

(21) Appl. No.: 14/728,599

(22) Filed: Jun. 2, 2015

(65) Prior Publication Data

US 2016/0355617 A1 Dec. 8, 2016

(51) Int. Cl.
*C08F 110/06* (2006.01)
*C07C 5/333* (2006.01)
*C07C 11/06* (2006.01)

(52) U.S. Cl.
CPC ............ *C08F 110/06* (2013.01); *C07C 5/333* (2013.01)

(58) Field of Classification Search
CPC ......... C07C 5/333; C07C 11/06; C08F 110/06
USPC ....................................................... 585/330
See application file for complete search history.

(56) References Cited

U.S. PATENT DOCUMENTS

| 5,750,800 A | 5/1998 | Marker et al. |
| 2010/0331589 A1* | 12/2010 | Zimmermann ........... C07C 5/05 585/314 |
| 2011/0049051 A1 | 3/2011 | Cougard et al. |

OTHER PUBLICATIONS

Chen, et al, "Case Studies on Optimum Reflux Ratio of Distillation Towers in Petroleum Refining Processes," Tamkang Journal of Science and Engineering, vol. 4, No. 2, 105-110, 2001.*
The International Search Report dated Sep. 29, 2016 in International Application No. PCT/US2016/032824.
Das, Mita, Membranes for olefin/paraffin separations. A Dissertation Presented to The Academic Faculty by Mita Das. In Partial Fulfillment of the Requirements for the Degree Doctor of Philosophy in the School of Chemical & Biomolecular Engineering. Georgia Institute of Technology, Dec. 2009.
Mauhar, S.M. et al, Optimization of Propylene—Propane Distillation Process. Chem. Pap., 2004, 58(6):pp. 386-390.

* cited by examiner

*Primary Examiner* — Fred M Teskin

(57) ABSTRACT

Processes for producing a polypropylene product by using a lower purity propylene stream. An operating parameter of the separation zone for a dehydrogenation zone effluent may be adjusted or controlled to lower the purity of the propylene stream produced by the separation zone. The reflux rate of propylene-propane splitter may be reduced. The duty of the reboiler for the propylene-propane splitter may be lowered. The number of stages in the propylene-propane splitter may be decreased.

16 Claims, 2 Drawing Sheets

POLYPROPYLENE PRODUCTION PROCESSES

FIELD OF THE INVENTION

Figure 1:
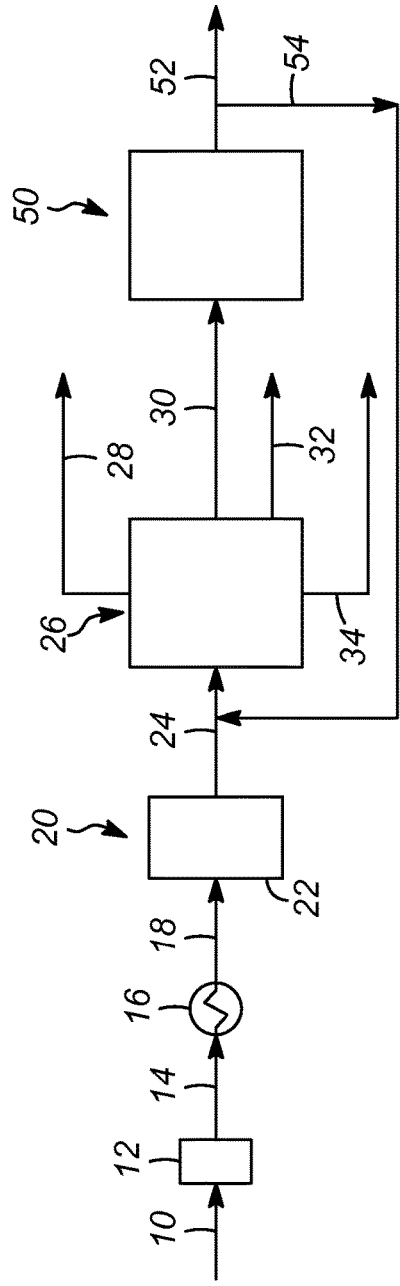

This invention relates generally to processes for the production of polypropylene and more particularly to processes for producing polypropylene from a stream of propylene separated from an effluent of a dehydrogenation zone.

BACKGROUND OF THE INVENTION

Propylene demand in the petrochemical industry has grown substantially, largely due to its use as a precursor in the production of polypropylene for packaging materials and other commercial products. Other downstream uses of propylene include the manufacture of acrylonitrile, acrylic acid, acrolein, propylene oxide and glycols, plasticizer oxo alcohols, cumene, isopropyl alcohol, and acetone.

Propylene is typically produced during the steam cracking or pyrolysis of hydrocarbon feedstocks such as natural gas, petroleum liquids, and carbonaceous materials (e.g., coal, recycled plastics, and organic materials), to produce ethylene. Additional sources of propylene are byproducts of fluid catalytic cracking (FCC) and reside fluid catalytic cracking (RFCC), normally targeting gasoline production. FCC is described, for example, in U.S. Pat. No. 4,288,688 and elsewhere. A mixed, olefinic C3/C4 hydrocarbon byproduct stream of FCC may be purified in propylene to polymer grade specifications by the separation of C4 hydrocarbons, propane, ethane, and other compounds.

More recently, the desire for propylene and other light olefins from alternative, non-petroleum based feeds has led to the use of oxygenates such as alcohols and, more particularly, methanol, ethanol, and higher alcohols or their derivatives. Methanol, in particular, is useful in a methanol-to-olefin (MTO) conversion process described, for example, in U.S. Pat. No. 5,914,433. The yield of light olefins from such a process may be improved using olefin cracking to convert some or all of the C4+ product of MTO in an olefin cracking reactor, as described in U.S. Pat. No. 7,268,265. Other processes for the targeted production of light olefins involve high severity catalytic cracking of naphtha and other hydrocarbon fractions. A catalytic naphtha cracking process of commercial importance is described in U.S. Pat. No. 6,867,341.

Paraffin dehydrogenation represents yet another dedicated route to light olefins and is described in U.S. Pat. No. 3,978,150 and elsewhere. However, the significant capital cost of a propane dehydrogenation plant is normally justified only in cases of large-scale propylene production units. The substantial supply of propane feedstock required to maintain this capacity is typically available from propane-rich liquefied petroleum gas (LPG) streams from gas plant sources.

From any of the foregoing processes, the propylene may be used to produce polypropylene. In order to produce polypropylene, the propylene must be in a stream typically has a purity of at least 99.5% by volume. However, some producers may not require such a high level of purity. For example, a purity of at least about 97% by volume (e.g., in the range from about 97% to about 99% by volume) or at least about 98% by volume (e.g., in the range from about 98% to about 99% by volume) may be acceptable for a non-polymer technology such as acrylonitrile production.

However, some polypropylene producers may be able to produce polypropylene from propylene having a purity lower than 99.5% by volume.

Therefore, it would be desirable to have one or more processes for producing polypropylene from a propylene stream having a purity below 99.5% by volume. It would be also desirable if such processes were economically viable.

SUMMARY OF THE INVENTION

One or more processes for the production of polypropylene have been invented in which the polypropylene is produced from a propylene stream having a purity less than 99.5% by volume. While the lower purity propylene may require additional energy in producing the polypropylene, the energy may be offset from adjustments to other process variables associated with producing the lower purity propylene.

In a first embodiment of the invention, the present invention may be broadly characterized as providing a process for producing polypropylene from a propylene stream comprising less than 99.5% by volume of polypropylene by: dehydrogenating a feed stream including propane in a dehydrogenation zone to provide an olefin steam, the olefin stream including propylene and propane; separating the olefin stream in a separation zone into a propylene stream and a propane stream, the propylene stream comprising less than 99.5% by volume of propylene; and, converting propylene from the propylene stream into polypropylene within a conversion zone.

In various embodiments of the present invention, the propylene stream comprises at least 95% by volume propylene.

In some embodiments of the present invention, the propylene stream comprises at between 97 and 95% by volume propylene.

In one or more embodiments of the present invention, the process further includes adjusting an operating parameter of the separation zone to lower a purity of the propylene stream. It is contemplated that the operating parameter comprises a reflux rate of the separation zone. It is also contemplated that the operating parameter comprises a number of stages in the separation zone.

In various embodiments of the present invention, the process further includes adjusting an operating parameter of the separation zone to lower a purity of the propylene stream and monitoring a purity of polypropylene from the conversion zone after the operating parameter of the separation zone has been lowered. It is contemplated that the process includes adjusting the operating parameter based upon the purity of the polypropylene. It is contemplated that the process also includes monitoring the purity of the polypropylene after the operating parameter of the separation zone has been adjusted based upon the purity of the polypropylene and adjusting the operating parameter of the separation zone to increase the purity of the propylene stream.

In a second aspect of the present invention, the present invention may be generally characterized as providing a process for producing polypropylene from a propylene stream comprising less than 99.5% by volume of polypropylene, the process comprising: passing a feed stream to a dehydrogenation zone including a catalyst and being configured to dehydrogenate propane in the feed stream and provide an olefin stream, the olefin stream including propylene and propane; passing the olefin stream to a separation zone having one or more columns being operated to separate a propylene stream from the olefin stream, the propylene stream comprising between 95 and 99.5% by volume of propylene; and, passing the propylene stream to a conversion zone being operated to convert propylene into polypropylene.

In various embodiments of the present invention, the propylene stream comprises between 95 and 97% by volume of propylene.

In various embodiments of the present invention, the process further includes adjusting an operating parameter of the separation zone to lower a purity of the propylene stream. It is contemplated that the operating parameter comprises a reflux rate of a column in the separation zone. It is further contemplated that the column comprises a propylene-propane splitter column. It is also contemplated that the operating parameter comprises a number of stages in a column in the separation zone. It is further contemplated that the column comprises a propylene-propane splitter column.

In some embodiments of the present invention, the process further includes adjusting an operating parameter of at least one column in the separation zone to lower a purity of the propylene stream and monitoring a purity of the polypropylene from the conversion zone after the operating parameter of the at least one column of the separation zone has been adjusted. It is contemplated that the process includes adjusting the operating parameter based upon the purity of the polypropylene to increase the purity of the propylene stream. It is further contemplated that the process includes monitoring the purity of the polypropylene after the purity of the propylene stream has been increased and adjusting the operating parameter of the at least one column of the separation zone to lower the purity of the propylene stream. It is even further contemplated that the at least one column of the separation zone comprises a propylene-propane splitter column.

Additional aspects, embodiments, and details of the invention, all of which may be combinable in any manner, are set forth in the following detailed description of the invention.

DETAILED DESCRIPTION OF THE DRAWINGS

Figure 2:
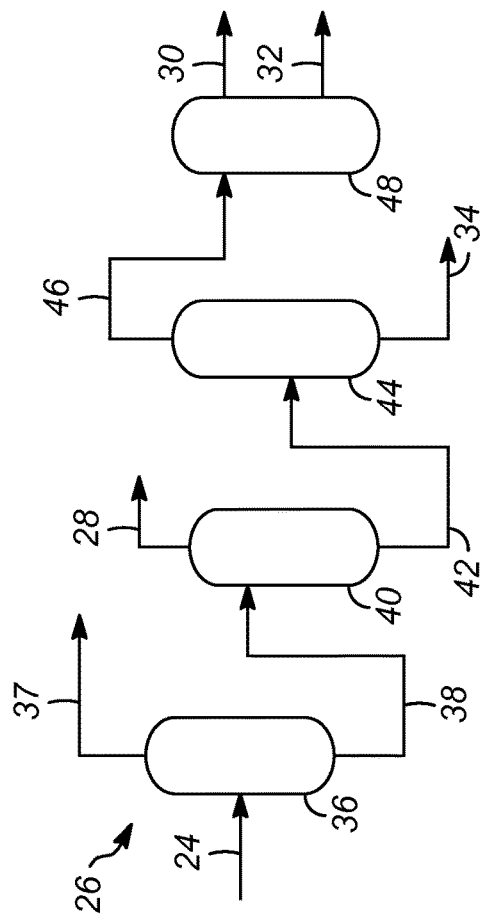
Figure 3:
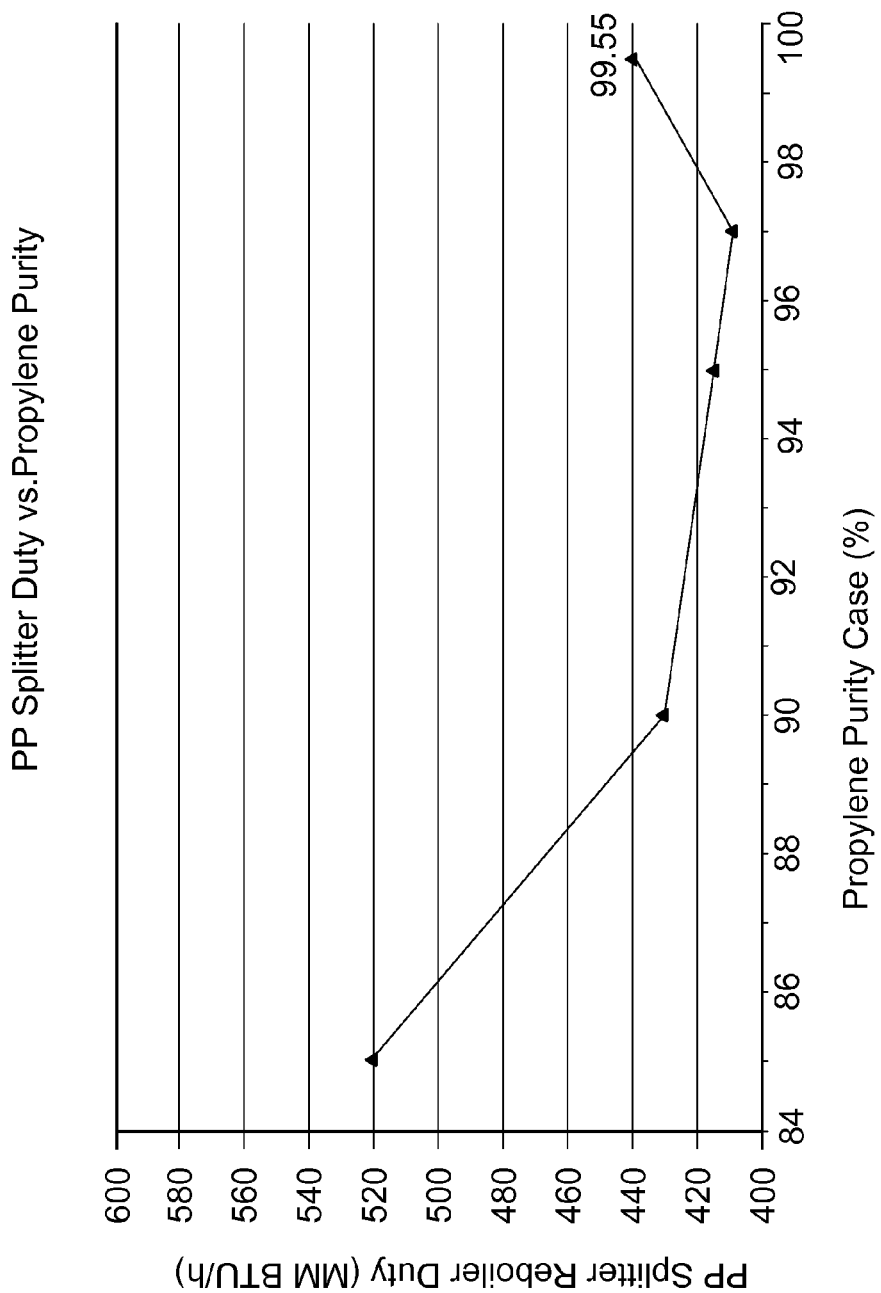

One or more exemplary embodiments of the present invention will be described below in conjunction with the following drawing figures, in which:

FIG. 1 shows a process flow diagram of one or more embodiments of the present invention; and, FIG. 2 shows an exemplary separation zone that can be used in association with various processes of the present invention; and, FIG. 3 shows a graphical comparison of the duty for a propylene-propane splitter column and the purity of the propylene stream.

DETAILED DESCRIPTION OF THE INVENTION

As mentioned above, processes for the production of propylene have been invented in which the propylene is used to produce polypropylene.

Unlike prior processes, the propylene stream has a purity below 99.5% by volume. Energy savings associated with producing the lower purity propylene stream is believed to offset, for example, the energy increase associated with the producing and separating the polypropylene.

With these general principles in mind, one or more embodiments of the present invention will be described with the understanding that the following description is not intended to be limiting.

As shown in FIG. 1, in various processes of the present invention, a feed stream 10 comprising a hydrocarbon gas rich in propane is passed through a dryer 12 to create a dry hydrocarbon stream 14. The dry hydrocarbon stream 14 may be passed to a heat exchanger 16 to cool reactor products from a recycle stream (discussed below) and preheat the dry hydrocarbon stream 14. From the heat exchanger 16, a preheated feed stream 18 may be passed to a dehydrogenation zone 20.

The dehydrogenation zone 20 includes at least one reactor 22 having a catalyst and being operated under conditions to produce an olefin stream 24 comprising propylene and propane. One commercially available propane dehydrogenation process is described in U.S. Pat. No. 3,978,150, herein incorporated by reference. As used herein, the term "zone" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

Some dehydrogenation processes use a noble metal catalyst on a support while other use a non-noble metal catalyst on a support. Exemplary supporting material includes zeolites. The synthesis of zeolites of the present invention can be formed by hydrothermal crystallization from a reaction mixture containing the desired amounts of silica and alumina and a templating agent. Zeolitic synthesis processes are known in the art, and can be found in U.S. Pat. No. 4,554,143; U.S. Pat. No. 4,440,871; U.S. Pat. No. 4,853,197; U.S. Pat. No. 4,793,984; U.S. Pat. No. 4,752,651 and U.S. Pat. No. 4,310,440, all of which are incorporated by reference. Another choice for the catalyst is a metal oxide stabilized zirconia or chomia. The metal in the metal oxide for stabilization can include metals such as scandium, yttrium, lanthanum, cerium, actinium, calcium, and magnesium. The catalyst may comprise small particles that are in the range of approximately 75 micrometers.

As is known, the reaction conditions include operation of the reactor at a temperature between 600 and 700° C., preferably between 630 and 650° C. The reaction conditions include a pressure at the reactor outlet in the range from 108 to 170 kPa (1 to 10 psig), or more preferably in the range from 122 to 136 kPa (3 to 5 psig). The reaction operates under an atmosphere comprising hydrogen, in addition to the hydrogen generated. The operation of the reactor 22 includes a hydrogen to hydrocarbon mole ratio at the reactor inlet in the range between 0.2 and 1, with a preferred hydrogen to hydrocarbon mole ratio at 0.6. The hydrogen generated in the dehydrogenation process, may be recovered and recycled to the feed stream 10.

The olefin stream 24 will comprise unreacted propane, propylene, hydrogen, and some non-selective reaction products (or byproducts) and can be passed to a separation zone 26. An optional selective hydrogenation zone (not shown) may be included to converts dienes and acetylenes to olefins. Such selective hydrogenation zone are known in the art.

In the separation zone 26, one or more distillation columns (described below) which separate the components of the olefin stream into one or more streams, including, a light ends stream 28, which may include hydrogen, a propylene stream 30, a propane stream 32, and a heavy stream 34. The term "column" means a distillation column or columns for separating one or more components of different volatilities.

Unless otherwise indicated, each column includes a condenser on an overhead of the column to condense and reflux a portion of an overhead stream back to the top of the column and a reboiler at a bottom of the column to vaporize and send a portion of a bottom stream back to the bottom of the column. Feeds to the columns may be preheated. The top pressure is the pressure of the overhead vapor at the outlet of the column. The bottom temperature is the liquid bottom outlet temperature. Overhead lines and bottom lines refer to the net lines from the column downstream of the reflux or reboil to the column.

For example, as shown in FIG. 2, the olefin stream 24 may be compressed and passed to a demethanizer column 36. In the demethanizer column 36, the components of the olefin stream 24 are fractionated, such as by conventional distillation, to provide a demethanizer overhead stream 37 predominantly comprising C1-hydrocarbons including methane, and also comprising hydrogen, carbon oxides, and nitrogen and a demethanized C2+ bottoms stream 38 comprising predominately propylene, and also comprising propane, ethylene, ethane, C4-dienes and acetylene. Herein, hydrocarbon molecules may be abbreviated C1, C2, C3 . . . Cn where "n" represents the number of carbon atoms in the one or more hydrocarbon molecules.

Furthermore, a superscript "+" or "−" may be used with an abbreviated one or more hydrocarbons notation, e.g., C3+ or C3−, which is inclusive of the abbreviated one or more hydrocarbons. As an example, the abbreviation "C3+" means one or more hydrocarbon molecules of three carbon atoms and/or more. The demethanized C2+ bottoms stream 38 may be passed to a second fractionation column, such as a deethanizer column 40.

In the deethanizer column 40, the components of the demethanized C2+ bottoms stream 38 are fractionated, such as by conventional distillation, to provide a deethanizer overhead stream comprising the light ends stream 28 (i.e., C2− hydrocarbons, including hydrogen, methane, acetylene, ethane, ethylene), and a deethanized C3+ bottoms stream 42 comprising predominately compounds heavier than ethane, such as propylene, propane, mixed butenes and/or butane. Although not depicted as such, the light ends stream 28 may be refined to recover one or more product streams, such as an ethylene stream.

The deethanized C3+ bottoms stream 42 or at least a portion thereof, may be passed to a depropanizer column 44. In the depropanizer column 44, the components of the deethanized C3+ bottoms stream 42 can be separated, or fractionated, such as by conventional distillation, to produce a depropanizer overhead stream 46 and a depropanized stream generally comprising C4+ components which is the heavy stream 34.

The depropanizer overhead stream 46 may be passed to a propylene-propane splitter column 48 to separate propylene (and methyl acetylene and propadiene) from propane. Thus, the propylene-propane splitter column 48 will provide the propylene stream 30 and the propane stream 32. The process can further include passing the propane stream 32 from the propylene-propane splitter column 48 to mix with the feed stream 10 as a recycle stream as mentioned above. Hydrocarbons heavier do not need to be separated from the streams, as they will be recycled back to the dehydrogenation zone 20. However, depending on the feedstock composition, in the presence of relatively large amounts of C4 and heavier hydrocarbons, the propane stream 32 can be passed through a depropanizer, with the heavier hydrocarbons passed to other process units, or recycled to the dehydrogenation zone 20.

Returning to FIG. 1, the propylene stream 30 may be passed from the separation zone 26 to a conversion zone 50 in which the propylene is contacted with a polypropylene forming catalyst to form a polypropylene rich effluent stream 52 which may be recovered and separated via known processes into a product polypropylene and a unreacted propylene stream 54 which may be passed back to the separation zone 26 by being combined with the olefin stream 24, for example, or by being passed directly to one or more columns within the separation zone 26, such as the depropanizer column 44 (not shown). Suitable catalysts are well known within the art and may comprise one or more Ziegler-Natia catalysts, conventional-type transition metal catalysts, metallocene catalysts, chromium catalysts, or vanadium catalysts, including one or more combinations thereof.

As mentioned above, it is believed that an acceptable polypropylene product can be made using a lower purity propylene stream. Accordingly, as shown in FIG. 3, a reboiler duty of a propylene-propane splitter was adjusted to provide varying purity levels of the propylene stream.

As can be seen in FIG. 3, a lower duty can be utilized to provide a propylene stream having a purity of at least 95% by volume propylene but less than 99.5% by volume. It is believed that the savings associated with having a lower purity propylene stream is offset from the increased energy associated with separating the propane and other non-propylene components from the polypropylene stream in the conversion zone and recycling it back to the separation zone, as discussed above. Nevertheless, the incremental increase in energy and costs associated with processing a 95 to 99% by volume propylene stream is believed to be less than the decrease in energy and operating costs associated producing and recycling a lower purity propylene stream.

Accordingly, in various embodiments, an operating parameter of the separation zone may be adjusted or controlled to lower the purity of the propylene stream. For example, the reflux rate of propylene-propane splitter may be reduced. Alternatively, the duty of the reboiler for the propylene-propane splitter may be lowered. Additionally, the number of stages in the propylene-propane splitter may be decreased. The parameter may comprise a combination of these enumerated parameters, or any other parameter that could be adjusted to provide the operating savings associated with a lower purity propylene stream.

The purity of the polypropylene product can be monitored to determine if the lower purity propylene stream is still at an acceptable level or if the energy savings from a lower purity propylene stream is now less than the increased cost associated with the operation of the conversion zone, the separation zone and/or both. If this is the case, the parameter could be adjusted again to increase the purity of the propylene stream. After doing so, the steps of monitoring and adjusting can be repeated so that the process is ongoing. Thus, after a certain amount of time, the parameter (or a different parameter) could be adjusted to once again lower the purity of the propylene stream.

By operating with a slightly lower purity propylene stream, the increased costs and energy associated with producing a polypropylene product will be offset as discussed above. By monitoring the polypropylene product, a polypropylene producer can ensure that the production is continually operating at proper operating conditions to minimize operating costs.

It should be appreciated and understood by those of ordinary skill in the art that various other components such as valves, pumps, filters, coolers, etc. were not shown in the drawings as it is believed that the specifics of same are well within the knowledge of those of ordinary skill in the art and a description of same is not necessary for practicing or understanding the embodiments of the present invention.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A process for producing polypropylene from a propylene stream comprising less than 99.5% by volume of polypropylene, the process comprising:
    dehydrogenating a feed stream including propane in a dehydrogenation zone to provide an olefin steam, the olefin stream including propylene and propane;
    separating the olefin stream in a separation zone into a propylene stream and a propane stream, the propylene stream comprising less than 99.5% by volume of propylene;
    converting propylene from the propylene stream into polypropylene within a conversion zone;
    adjusting an operating parameter of the separation zone to lower a purity of the propylene stream; and,
    monitoring a purity of polypropylene from the conversion zone after the operating parameter of the separation zone has been adjusted.

2. The process of claim 1 wherein the propylene stream comprises at least 95% by volume propylene.

3. The process of claim 1 wherein the propylene stream comprises at between 97 and 95% by volume propylene.

4. The process of claim 1 wherein the operating parameter comprises a reflux rate of the separation zone.

5. The process of claim 1 wherein the operating parameter comprises a number of stages in the separation zone.

6. The process of claim 1 further comprising:
    adjusting the operating parameter based upon the purity of the polypropylene.

7. The process of claim 6 further comprising:
    monitoring the purity of the polypropylene after the operating parameter of the separation zone has been adjusted based upon the purity of the polypropylene; and,
    adjusting the operating parameter of the separation zone to increase the purity of the propylene stream.

8. A process for producing polypropylene from a propylene stream comprising less than 99.5% by volume of polypropylene, the process comprising:
    passing a feed stream to a dehydrogenation zone including a catalyst and being configured to dehydrogenate propane in the feed stream and provide an olefin stream, the olefin stream including propylene and propane;
    passing the olefin stream to a separation zone having one or more columns being operated to separate a propylene stream from the olefin stream, the propylene stream comprising between 95 and 99.5% by volume of propylene;
    passing the propylene stream to a conversion zone being operated to convert propylene into polypropylene;
    adjusting an operating parameter of at least one column in the separation zone to lower a purity of the propylene stream; and,
    monitoring a purity of the polypropylene from the conversion zone after the operating parameter of the at least one column of the separation zone has been adjusted.

9. The process of claim 8 wherein the propylene stream comprises between 95 and 97% by volume of propylene.

10. The process of claim 8 wherein the operating parameter comprises a reflux rate of a column in the separation zone.

11. The process of claim 10 wherein the column comprises a propylene-propane splitter column.

12. The process of claim 8 wherein the operating parameter comprises a number of stages in a column in the separation zone.

13. The process of claim 12 wherein the column comprises a propylene-propane splitter column.

14. The process of claim 8 further comprising:
    adjusting the operating parameter based upon the purity of the polypropylene to increase the purity of the propylene stream.

15. The process of claim 14 further comprising:
    monitoring the purity of the polypropylene after the purity of the propylene stream has been increased; and,
    adjusting the operating parameter of the at least one column of the separation zone to lower the purity of the propylene stream.

16. The process of claim 15 wherein the at least one column of the separation zone comprises a propylene-propane splitter column.

* * * * *